United States Patent

McShane

[11] Patent Number: 6,149,624
[45] Date of Patent: Nov. 21, 2000

[54] APPARATUS AND METHOD FOR THE RAPID INDUCTION OF HYPOTHERMIC BRAIN PRESERVATION

[76] Inventor: Richard Houston McShane, 92 Mountain Ave., Llewellyn Park, West Orange, N.J. 07052

[21] Appl. No.: 09/019,373

[22] Filed: Feb. 5, 1998

[51] Int. Cl.$^7$ .......................................................... A61F 7/12
[52] U.S. Cl. ........................... 604/113; 604/506; 604/514
[58] Field of Search ................................ 604/54, 19, 35, 604/43, 44, 51, 53, 93, 113, 114, 506, 514; 607/104, 105

[56] References Cited

U.S. PATENT DOCUMENTS

| | | | |
|---|---|---|---|
| 3,406,531 | 10/1968 | Swenson et al. | 607/105 |
| 3,504,674 | 4/1970 | Swenson et al. | 607/105 |
| 3,982,540 | 9/1976 | Ross | 128/278 |
| 4,747,826 | 5/1988 | Sassano | 604/51 |
| 4,874,359 | 10/1989 | White et al. | 604/4 |
| 5,002,528 | 3/1991 | Palestrant | 604/28 |
| 5,077,980 | 1/1992 | Weber | 607/105 |
| 5,269,756 | 12/1993 | Dryden | 604/54 |
| 5,540,841 | 7/1996 | Gsell et al. | 604/56 |
| 5,685,843 | 11/1997 | Enhorning | 604/54 |
| 5,779,662 | 7/1998 | Berman | 604/22 |

*Primary Examiner*—Wynn Wood Coggins
*Assistant Examiner*—Sharon Finkel
*Attorney, Agent, or Firm*—Thomas A. Beck

[57] ABSTRACT

Apparatus and method for using a cooled fluid to be introduced into the lungs as a heat exchange which as a result of the circulatory system of the body, lowers the temperature of the brain as well as the temper of the body in general. In instances where cardiopulmonary arrest occurs and CPR is delayed due to the clinical setting in which the arrest takes place, the rapid induction of brain hypothermia by liquid pulmonary lavage secures valuable time for the subsequent application of CPR techniques. The method can be used on any elective hypothermic surgery.

16 Claims, 3 Drawing Sheets

APPARATUS AND METHOD FOR THE RAPID INDUCTION OF HYPOTHERMIC BRAIN PRESERVATION

BACKGROUND OF THE INVENTION

1. Technical Field of the Invention

The present invention relates generally to an apparatus and method for providing hypothermic brain preservation in instances where pulmonary or cardiac dysfunction has occurred.

2. Description of the Related Art

The human body requires oxygen in order to sustain itself. The heart and lungs provide means for providing the oxygen to the other parts of the body. They work together to supply body tissues with life giving oxygen. Air, the body's source of oxygen, is carried to the lungs by breathing. Oxygen in the inhaled air is absorbed into the blood and then pumped to the heart by means of the circulatory system. The circulatory system has a double loop since initially blood is pumped from two chambers of the four chambered heart via the pulmonary artery to a network of capillaries in the lungs which enrich the blood with oxygen. The oxygen rich blood then travels back to the heart via the pulmonary vein to the two other chambers of the four chambered heart whereupon the oxygenated blood is pumped from the heart ventricle via the aorta to networks of capillaries to transfer oxygen to the body tissues and organs. After travelling through the network of capillaries that form the circulatory system connected to tissues and organs, the oxygen depleted blood travels back to the heart via the vena cavae. The process is then repeated. The keystone to the circulation is the heart. Without the heart pumping, the blood will not circulate, and the tissues and organs that require oxygen will cease to function. A particularly vital recipient of the oxygenated blood supply is the brain. The brain receives 25% or more of the body circulation of cardiac output. If a person has suffered a cardiac arrest and as a result, has experienced a cessation of heartbeat and cardiac function, there is a limited amount time to rectify the situation before irreversible damage occurs, especially in the brain. The brain is particularly sensitive to oxygen. In certain situations when the lungs are deprived of oxygen, the blood does not get oxygenated, and the brain is deprived of oxygen. Again in this situation, reversible and irreversible brain damage occurs.

In recent years, the medical profession has developed emergency resuscitation techniques performed at the scene of a cardiopulmonary event. At this time the lungs and/or heart are failing and the resuscitative procedures are performed. Some cardiac action almost invariably persists and when this cardiac action is not present a rhythmic compression of the heart and chest is performed to maintain circulation. This procedure is known as cardiopulmonary resuscitation (CPR). The technique is used to start the heart pumping and to restore the flow of oxygen rich blood. When this action commences timely, the person can survive the episode.

The presence of permanent brain damage, as more specifically set forth below, is the point of no return during cardiopulmonary resuscitation.

If the brain is starved of oxygen, brain damage spreads throughout the cortex or surface areas of the brain. As a result, a decorticate condition develops eliminating motor and sensory functions and leaving the central brain and brain stem to function at a very basic level maintaining a basal heart rate and basal respiratory drive. In CPR, the clinical presence of fixed dilated pupils (FDP) identifies the loss of a very protective reflex. Fixed dilated pupils do not respond to external stimuli such as light, that is, the pupils are fixed. For many years, FDP have been used clinically to guide physicians and health care personnel in making medical decisions as to the state of the health of the patient. In most instances, the finding of FDP gives rise to an inference of or confirms the presence of brain damage. The finding of FDP along with absent peripheral pulses and no evidence of a beating heart may lead to the suspension of efforts and an acceptance of death. Irrevocable treatment decisions must be made in a few seconds and the determination and its consequences may result in irreversible brain damage.

There are instances in which individuals who displayed FDP were successfully resuscitated. A variety of CPR methods were used depending upon the cause of cardiac or pulmonary failure. In successful CPR, external massage has been associated with the return of the pupillary light reflex during rhythmic chest and cardiac compression. If the benefit or efficiency of CPR is lost, FDP returns. The pupils are in the clinical setting, an effective monitor of the efficiency of CPR Clinical experience in the field has repeatedly demonstrated that fixed dilated pupils do not necessarily indicate that permanent brain damage is present. Some medical authorities have concluded that FDP are a grave warning, but are not necessarily an irrevocable indicator of the point of no return.

There have been a number of clinical situations wherein the hypothermic state, with its abnormally low temperature, has been associated with FDP and no trace of radial artery and femoral artery pulses only to find a slowly beating heart and a palpable carotid pulse. The brain is more susceptible to reversible and subsequently irreversible damage than the heart and lungs. Therefore, the brain usually suffers irreversible damage before the heart and lungs become irretrievable.

However, numerous anecdotal reports of successful hypothermic resuscitations using traditional techniques have been followed by memory loss or other subtle indications of brain damage. On the other hand, hypothermic anesthesia techniques to levels of 15° C. create a window of one hour or more for elective brain surgery. These hypothermia techniques clearly protect brain function.

In 1991, researchers developed partial liquid ventilation (PLV). In this procedure, the lungs are partially filled with perfluorocarbons while the remaining portion of the pulmonary tree are ventilated with fresh oxygen which is pumped into the remaining open always using a conventional ventilator. In the PLV procedure, perfluorocarbons have been utilized in the lungs in situations where oxygen was carried to the pulmonary tree by dissolving the oxygen in the perfluorocarbons and ventilating the lungs with oxygen rich perfluorocarbon solution. This procedure differs from the present invention in that the present invention uses a cooled fluid to provide rapid hypothermic brain protection as a part of cardiopulmonary resuscitation when FDP are first noted; whereas the PLV method uses the fluorocarbons in the lungs, but for a totally different purpose. In PLV, the fluid, containing oxygen, aids the air sacs in the lungs which have collapsed.

The proposed method of hypothermic brain preservation (HBP) differs significantly from PLV in that the lungs must be completely filled with a friendly fluid, not necessarily perfluorocarbons, to induce hypothermia and have brain preservation. In HBP the primary goal is to remove calories from the brain and lower the brains temperature in order to provide a greater period of time during which heart and lung function can be restored by a variety of methods and/or techniques.

Other objects and features as well as additional details of the present invention will become apparent from the following detailed description and annexed drawings of the presently preferred embodiments thereof, when considered in conjunction with the associated drawings.

SUMMARY OF THE INVENTION

The present invention provides an apparatus and method for using a cooled fluid to be introduced into the lungs as a heat exchange which as a result of the circulatory system of the body, lowers the temperature of the brain as well as the temperature of the body in general. Heat exchange is more efficient with liquids than gases. Liquids traditionally carry calories more efficiently than gases.

All the blood within the body travelling to the brain passes through the pulmonary circuit first. In this instance the lungs act as an extremely efficient heat exchanger.

The system embodied with the present invention comprises a reservoir containing a fluid that is friendly to the lungs and may be oxygen enriched. The fluid/liquid used in accordance with the present invention is a composition/compound which is friendly to the pulmonary mucosa. Because the fluid is instilled into the body, it must be non-toxic to the system and must not detrimentally accumulate in the various organs of the body. In addition to being non-toxic, it must have good heat exchange properties for cooling areas within the body and carrying away the heat from the area that it contacts; it must have the capacity to carry oxygen dissolved therein into the lungs to react with hemoglobin, and to absorb carbon dioxide within the system and carry the carbon dioxide away when the fluid, a pulmonary lavage, is withdrawn from the body.

The fluid (liquid lavage) may conveniently be a chemically inert, non-toxic composition such as an isotonic saline solution which will not deplete surfactants in the system. Also especially useful are the family of compounds known as perfluorocarbons. Perfluorocarbons are compounds comprising carbon, fluorine and hydrogen, although they may contain other atoms such as oxygen, nitrogen and even bromine. The perfluorocarbons are useful in the present invention because they have properties similar to human blood, i.e. they act as a solvent for all common gases. To commence the cycle, the fluid is carried from the reservoir to cooling means which lowers the temperature of the fluid. The cooled fluid is then directed and introduced into the lungs of the individual via a first catheter means for transporting the fluid. In the lungs, the fluid immediately cools the blood by means of the heat exchange between the cooled fluid in the lungs and the blood passing through the pulmonary circuit. The blood travels from the pulmonary vein to the left heart. The fluid is withdrawn from the lungs from a second transport means.

As noted, the lungs act as a heat exchange thereby cooling the blood. Because the cooled fluid contacts the lungs, the temperature of the blood passing through the lungs is lowered substantially. The cooled blood travels to the left heart and thence to the other areas of the body from the left ventricle through the aorta and the capillaries. The cooled blood flows to the brain where its cooling immediately protects the brain from injury. Natural body mechanisms produce vasoconstriction in other parts of the body and selectively shunt the cooled blood preferentially to the brain.

The apparatus assembly of the present invention is suitable for inducing rapid hypothermic brain preservation using a liquid pulmonary lavage and comprises several cooperating units. More particularly, the assembly comprises a reservoir suitable for storage of a liquid pulmonary lavage. The reservoir is connected to heat exchanger means suitable for cooling. Extending from the reservoir/heat exchanger unit is a first flexible catheter having a distal end suitable for dispensing and instilling said cooled liquid pulmonary lavage into a subject's tracheobronchial tree. There is also a second flexible catheter also inserted in said subject's tracheobronchial tree substantially parallel to said first catheter and having a closed distal end and a proximal end, and having a plurality of openings adjacent said proximal end of said catheter, said openings providing access to the interior of said catheter. From these openings the effluent is withdrawn from the body of the subject and is passed to an effluent reservoir. The effluent reservoir contains means for creating low pressure in the second catheter to withdraw said liquid pulmonary lavage effluent from the subject's tracheobronchial tree. The effluent reservoir has means to filter and purify the liquid pulmonary lavage effluent to form a recycled liquid pulmonary lavage effluent. The reprocessed liquid pulmonary lavage is then passed into the fluid reservoir from which the cycle is repeated.

DETAILED DESCRIPTION OF THE PRESENTLY PREFERRED EMBODIMENTS

It has been experimentally and clinically determined for the purposes of the present invention that many methods of hypothermic induction cold water immersion, peritoneal lavage, rectal lavage, packing the head with ice have proved to be too slow to provide brain protection. The proposed apparatus assembly and method of the present invention induces hypothermia by utilizing a vascular bed through which the body's entire blood supply circulates, the pulmonary circuit.

Rapid hypothermic brain protection in accordance with the present invention can be used deliberately as an integral part of cardiopulmonary resuscitation when fixed pupils are first noted. The method and apparatus of the present invention can also be conveniently used in any type of existing hypothermic surgery.

In instances when a CPR procedure is indicated, fifteen to sixty minutes, and possibly more time may be required to correct a failed heart pump or failing pulmonary tree. By using the lungs as a means to transfer sensible heat between two fluids without a change of state taking place, according to traditional thermodynamic principles, a massive caloric depletion has been found to drop the temperature of the body system up to 7° C. in one to three minutes.

In instances where cardiopulmonary arrest occurs and is delayed due to the clinical setting in which the arrest takes place, the rapid induction of brain hypothermia by liquid pulmonary lavage pursuant to the apparatus and method of the present invention secures valuable time for the subsequent application of current surgical techniques or CPR and other resuscitative techniques that have in the past been precluded by brain damage.

Figure 1:
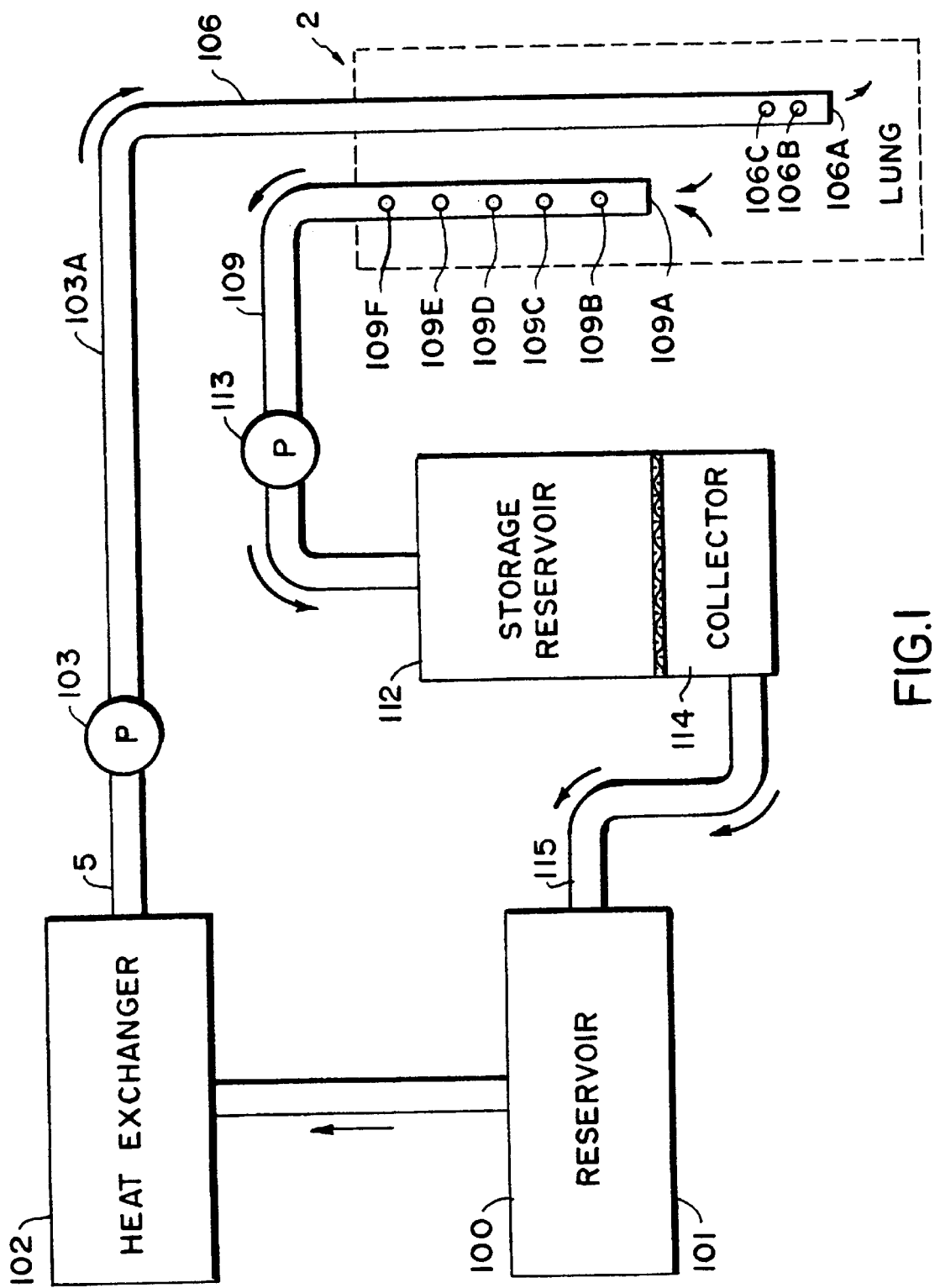
FIG. 1 depicts the apparatus assembly of the present invention.

Referring to the drawings, FIG. 1 is a depiction of the components comprising the apparatus assembly of the present invention.

In using the method and apparatus of the present invention, calorie depletion is effected using a semi-closed liquid tracheobronchial loop. In another embodiment of the present invention, caloric depletion occurs with a single and/or multiple instillation into the tracheobronchial tree. In the latter, the fluid is administered by a transtracheal or cricothyroid catheter in specific doses sufficient to fill the tracheobronchial tree.

The fluid dosage instilled into the subject in accordance with the present invention is computed according to the formula:

Dose (total pulmonary capacity in cc's of fluid=25 cc fluid×Kg body weight.

In the embodiments noted above, a hypothermic package of liquid is provided as an emergency device that involves a cricothyroidotomy with a 5 French multi-holed catheter placed deep in the right mainstream bronchus. Each hypothermic package contains 750 cc of liquid or roughly half of the total volume of the tracheobronchial tree of a 70 Kg man.

In the semi-closed loop, a suction retrieval system removes noncardiac pulmonary edema (NCPE) and cellular debris which mechanically obstructs respiration. This NCPE and debris characteristically floats on the surface of the cool fluid in the tracheobronchial tree.

Using the method of the present invention, CPR is an integral part of the resuscitative event. As with the traditional external cardiac massage, the air in the air-filled chest is compressible and therefore decreases the efficiency of the external cardiac massage. During the procedure as detailed herein, the pulmonary tree is filled with fluid which is therefore not compressible, and the efficiency of the external cardiac massage improves. This is an unanticipated and substantial benefit to resuscitation.

The structure of the apparatus of the present invention is depicted generally in FIG. 1. Fluid 101, such as a 0.9% saline solution, is contained in reservoir 100 which is connected to heat exchanger means 102 in which fluid 101 is cooled to form fluid 5. Cooled fluid 5 is pumped from heat exchanger 102 via pumping means 103 via tube means 103A into lung circulatory system depicted by the broken line rectangle 2, thence to the deepest point in lung circulatory system 2 by tube or catheter 106. Tube 106 has an open end 106A and openings 106B and 106C to allow cooled fluid 5 to circulate within the body and cool the brain as set forth in greater detail hereinafter. After fluid 5 has circulated to contact the blood that is to flow to the brain, it remains in the lung circulatory system 2 and is designated 5' to distinguish it from the fluid 5 that was cooled and originally circulated to lung circulatory system 2.

Tube 109 having open end 109A removes debris and non cardiac pulmonary edema (NCPE) froth from lung system 2 by suction means and deposits said debris and NCPE in storage reservoir 112. Fluid 5' emerges from the body having been warmed by the body heat to a temperature above the temperature at which it enters the body after treatment in heat exchanger 102. Tube 109 has an open end 109A and multiple side ports 109B, 109C, 109D, 109E and 109F which collect the liquid pulmonary lavage fluid passing from lung system 2 as a result of low pressure means, such as vacuum pump 113, to draw effluent fluid 5' from the body and dispense same into storage area 112. Storage reservoir 112 contains separation means within it to separate the edema NCPE froth from effluent fluid 5 so that it is collected in section 114 of the reservoir, filtered, purified and recycled via connecting tube 115 to reservoir 100 for reuse. In the apparatus, the filtered fluid is returned to the reservoir thus creating a semi-closed circuit.

It is important to emphasize that the fluids that can be used in accordance with the present invention can be easily characterized by virtue of their properties. Any fluid/liquid is suitable for use in the method of the present invention provided it is: non-toxic to the system; chemically inert as to the human system and does not detrimentally accumulate in the organs of the body; an efficient heat exchange fluid; and friendly to the pulmonary mucosa, i.e. all of the above. Further, the fluids are stable and will not decompose upon exposure to the internal pH of the body, and which will not upset the body chemistry.

Several preferred fluids suitable for use in the present invention comprise typical saline solutions presently commercially available, as well as the family of perfluorocarbons disclosed hereinafter. Fluids that can be used in accordance with the present invention chemically inert, non-toxic compositions which are stable and will not decompose upon exposure to the internal pH of the body, and which will not upset the body chemistry.

The saline solution which is used in accordance with the present invention is a typical commercially available solution of distilled water and sodium chloride. A 0.9% solution of sodium chloride is considered isotonic to the body. A normal saline solution (i.e., one having an osmolality similar to blood serum) consists of 0.85% salt solution, which is necessary to maintain the osmotic pressure and the stimulation and regulation of muscular activity. Obviously, hypertonic and hypotonic saline solutions can be used satisfactorily.

Any solution that has a concentration of electrolytes, nonelectrolytes or a combination of the two that will exert equivalent osmotic pressure in comparison with the blood in the human system can also be used. For example either a 0.16 molar sodium chloride solution (approximately 0.95% salt in water) or 0.3 molar nonelectrolyte is approximately isotonic with human red blood cells.

The perfluororcarbon compounds used in accordance with the present invention have an ideal property of being an excellent solvent for gases. For example 45 mL of oxygen will dissolve in 100 mL of perfluorocarbon fluid. Carbon dioxide is approximately 2.5 times more soluble than is oxygen.

Perfluorocarbons are generally insoluble in other liquids and therefore must be emulsified with a suitable emulsifier called a surfactant. The surfactant used in combination with the perfluororcarbons is conveniently based upon a phospholipid.

Lipids are compounds that are produced by living organisms and are virtually insoluble in water but are soluble in non-polar solvents. Phospholipids are nonpolar substances containing one or more phosphate residues. Many also possess one or more fatty acid residues. The glycerophospholipids (phosphoglycerides) are the most abundant members of the class. The simplest glycerophospholipids are the phosphatidic acid, diacylglycerols joined to phosphoric acid through an ester link. Salts of phosphatidic acid, known as phosphatides, predominate at physiological pH. The unique phosphatides that have been characterized differ only in their fatty acid residues. The subclasses of glycerophospholipids are the phosphatidylcholines, phosphatidylethanolamines, phosphatidylinositols, and phosphatidylserine.

These phospholipids are amphipathic containing the polar "heads" that help the fluid dissolve in water so hat it will be compatible with plasma. It also has the nonpolar "tails" that tend to aggregate in aqueous environment. The formation of the micelles and liposomes make the fluid compatible with the organs and tissues that it contacts.

Perfluorocarbon-surfactant mixture per se needs additional additives because this mixture contains little osmotic and oncotic pressure. It is thus necessary to add electrolytes and volume expanders to fulfill these requirements.

The total composition for the fluid thus includes from about 20% to about 30% of the perfluorocarbons as the gas transport element, 1–3% w/v surfactant which serves as a emulsifier, an oncotic agent such as hydroxyethyl cellulose, salts for adjusting osmotic pressure such as NaCl, KCl, $MgCl_2$, $CaCl_2$, $NaH_2PO_4$, a buffer such as $NaHCO_3$ and water. Obviously the amounts of the constituents are illustrative and will vary depending upon the subject and other factors readily apparent to those skilled in the art.

A preferred perfluorocarbon is Fluorosol DA, manufactured by Green Cross. It is a mixture of seven parts perfluorodecalin (perfluorodecahydronaphthalene), 3 parts perfluorotripropylamine, 2.7% Pluronic F-68, (a family of polymers of polyoxypropylene with polyoxyethylene usually at each end thereof) and about 0.4% phospholipid prepared from for example, egg yolk, to form the membrane coating for the emulsion.

The perfluorocarbon composition behaves as an artificial blood and has the advantage of not needing to be cross matched and screened for diseases and has a much longer shelf life than the 35 days of human blood. A substantial advantage is that it can dissolve three times as much oxygen as human blood.

Figure 2:
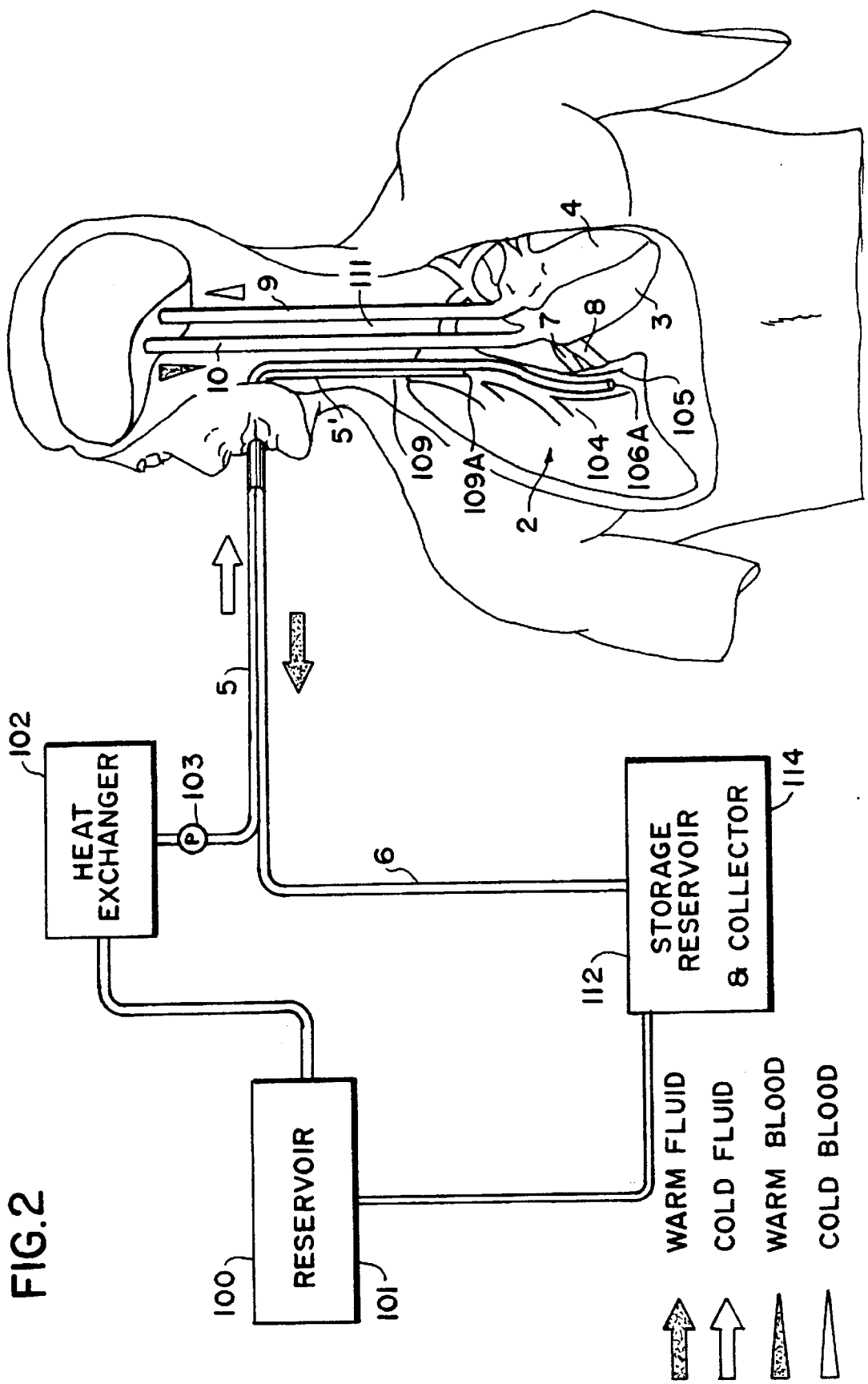
FIG. 2 is a view of the assembly as used in conjunction with a human subject according to the method of the present invention.

Referring to FIG. 2, fluid 101 passes from reservoir 100 to heat exchanger means 102 in which fluid 101 is cooled. After cooling, cooled fluid 5 emanates from heat exchanger 102 and flows via pumping means 103 into lung circulatory bed 2, thence to the deepest point in the pulmonary tree 104, the right main stem bronchus 105, by a tube 106. Tube 106 possesses open bottom 106A and multiple side ports 106B and 108C.

Further, with respect to FIG. 2, a tube 109 having open end 109A removes debris and non cardiac pulmonary edema (NCPE) froth from the upper trachea 111 by suction means and deposits said debris and NCPE in storage reservoir 112. During the procedure the patient is maintained in an upright position and the higher specific gravity of cold fluid 5 floats the debris and NCPE to upper airway 113 where it is removed in conjunction with warm fluid 5'.

The blood coursing through lung circulatory bed 2 is cooled substantially by its exposure to cold fluid 5. The cooled blood flows via pulmonary vein 8 to ventricle 4 on the left side of the heart. The cooled blood flows through the carotid arteries 9 to the brain 1. The flow of blood from the heart to the brain represents about 25% of the total cardiac output. Brain 1 is cooled and the thermodynamics of the system result in warming of the blood and concomitant cooling of brain 1. The warm blood 5' emerging from brain 1 flows via the superior vena cava 10. The left side of the heart ventricle 3 pumps the warm blood via the pulmonary artery 7 to lung vascular tree 2 for caloric exchange.

Figure 3:
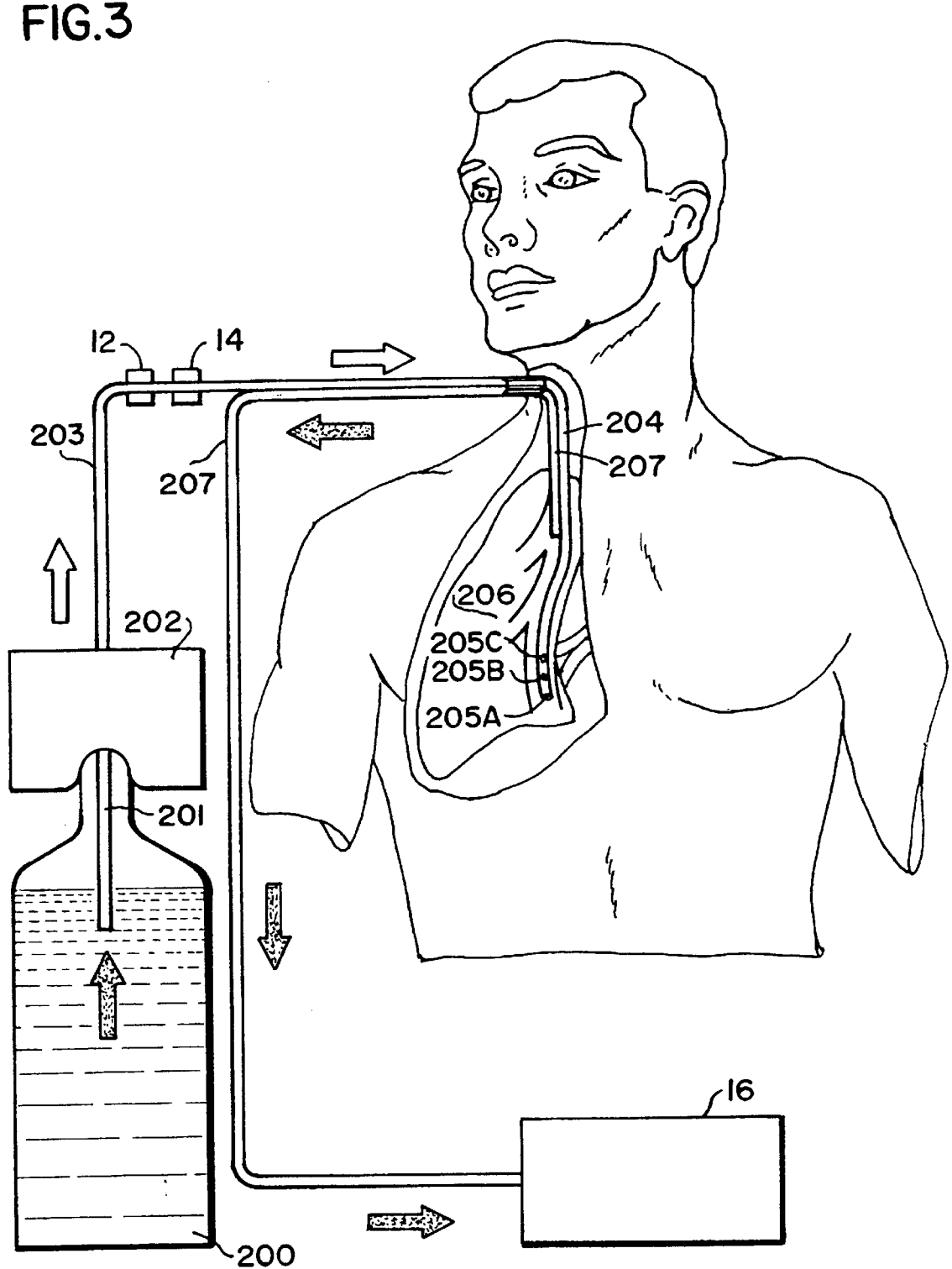
FIG. 3 is a view of a specific embodiment of the present assembly.

FIG. 3 depicts a simplified embodiment of the present invention which can be conveniently used in a portable application. Container 200 containing liquid 201 passes through a cooling pack 202 through catheter tube 203 to catheter 204 with openings 205A, B, C in lung circulatory bed 206. Catheter 207 is set in place adjacent to catheter 204 in lung circulatory bed 206 and withdraws the debris and NCPE froth from the upper trachea by suction means (not shown). This assembly uses essential components to rapidly induce hypothermic brain preservation.

Thus, while there have been shown and described and pointed out fundamental novel features of the invention as applied to currently preferred embodiments thereof, it will be understood that various omissions and substitutions and changes in the form and details of the method and assembly illustrated, and in their operation, may be made by those skilled in the art without departing from the spirit of the invention. In addition it is to be understood that the drawings are not necessarily drawn to scale but that they are merely conceptual in nature. The invention is not limited by the embodiments described above which are presented as examples only but can be modified in various ways within the scope of protection defined by the appended patent claims.

In instances where cardiopulmonary arrest occurs and CPR is delayed due to the clinical setting in which the arrest takes place, the rapid induction of brain hypothermia by liquid pulmonary lavage secures valuable time for the subsequent application of CPR techniques. The method can also be used on any elective medical applications.

I claim:

1. An assembly suitable for inducing rapid hypothermic brain preservation using a liquid pulmonary lavage comprising:

a fluid reservoir suitable for storage of a liquid pulmonary lavage;

heat exchanger means suitable for cooling said liquid pulmonary lavage;

means connecting said fluid reservoir and said heat exchanger means;

means associated with said fluid reservoir for circulating said liquid pulmonary lavage and connected to, a first flexible catheter extending from and connected at its proximal end to said heat exchanger means and having a distal end suitable for dispensing said cooled liquid pulmonary lavage in a subject's tracheobronchial tree;

a second flexible catheter insertable in said subject's tracheobronchial tree positioned substantially parallel to said first catheter and having a closed distal end and a proximal end, and having a plurality of openings adjacent said proximal end of said catheter, said openings providing access to the interior of said catheter;

said proximal end of said second catheter connected to an effluent reservoir;

said effluent reservoir containing means for creating low pressure in said second catheter to withdraw said liquid pulmonary lavage effluent from the subject's tracheobronchial tree; said effluent reservoir having means to filter and purify said liquid pulmonary lavage effluent to form a recycled liquid pulmonary lavage effluent;

means connecting said effluent reservoir and said fluid reservoir to deliver said recycled liquid pulmonary lavage effluent thereto.

2. The assembly suitable for inducing rapid hypothermic brain preservation using the liquid pulmonary lavage defined in claim 1 further including the liquid pulmonary lavage in a dosage amount to be instilled into said subject according to the formula 25 cc of said liquid pulmonary lavage for each kilogram of the subject's body weight.

3. The assembly suitable for inducing rapid hypothermic brain preservation using the liquid pulmonary lavage defined in claim 2, wherein said liquid pulmonary lavage comprises an isotonic saline solution.

4. The assembly suitable for inducing rapid hypothermic brain preservation using the liquid pulmonary lavage defined in claim 2, wherein said liquid pulmonary lavage comprises a hypertonic solution.

5. The assembly suitable for inducing rapid hypothermic brain preservation using the liquid pulmonary lavage defined in claim 2, wherein said liquid pulmonary lavage comprises a hypotonic solution.

6. The assembly suitable for inducing rapid hypothermic brain preservation using the liquid pulmonary lavage defined in claim 2, wherein said liquid pulmonary lavage comprises a nonelectrolyte which is isotonic with human red blood cells.

7. The assembly suitable for inducing rapid hypothermic brain preservation using the liquid pulmonary lavage defined in claim 2, wherein said liquid pulmonary lavage comprises a perfluorocarbon and a surfactant.

8. The assembly suitable for inducing rapid hypothermic brain preservation using the liquid pulmonary lavage defined in claim 7, wherein said surfactant is based upon a phospholipid.

9. The assembly suitable for inducing rapid hypothermic brain preservation using the liquid pulmonary lavage defined in claim 8, wherein said phospholipid is at least one glycerophospholipid.

10. The assembly suitable for inducing rapid hypothermic brain preservation using the liquid pulmonary lavage defined in claim 9, wherein said at least one glycerophospholipid is selected from the group consisting of phosphatidic acid, diacylglycerols joined to phosphoric acid through an ester link.

11. The assembly suitable for inducing rapid hypothermic brain preservation using the liquid pulmonary lavage defined in claim 9, wherein said at least one glycerophospholipid is selected from the group consisting of phosphatidylcholines, phosphatidylethanolamines, phosphatidylinositols and phosphatidylserine.

12. The assembly suitable for inducing rapid hypothermic brain preservation using the liquid pulmonary lavage defined in claim 11, wherein said dosage comprises 20% to 30% perfluorocarbon, between about 1% and 3% w/v surfactant, an oncontic agent, salts for adjusting the osmotic pressure selected from the group consisting of NaCl, KCl, $MgCl_2$, $CaCl_2$, $NaH_2 PO_4$, $NaHCO_3$ buffer and water.

13. The assembly suitable for inducing rapid hypothermic brain preservation using the liquid pulmonary lavage defined in claim 12, wherein said perfluorocarbon is a mixture of seven parts perfluorodecahydronaphthalene, 3 parts perfluorotripropylamine, 2.7% a blend of polymers of polyoxypropylene with polyoxyethylene predominately at each end thereof, and about 0.4% phospholipid.

14. The assembly suitable for inducing rapid hypothermic brain preservation using the liquid pulmonary lavage defined in claim 13, wherein said phospholipid is made from egg yolk to form a membrane coating for an emulsion formed.

15. A method for the rapid induction of brain preservation comprising:

passing a liquid suitable for use as a pulmonary lavage from a reservoir through heat exchanger means suitable for cooling said liquid pulmonary lavage into a first flexible catheter extending from and connected at its proximal end to said heat exchanger means and having an open distal end suitable for dispensing said cooled liquid pulmonary lavage;

inserting said distal end into a subject's tracheobronchial tree and passing said liquid pulmonary lavage into said tracheobronchial tree so that said cooled liquid is pumped to the deepest part of the subject's pulmonary tree with the result that the blood circulating through the lungs is cooled which flows to the heart and the brain, thereby cooling the brain;

said liquid pulmonary lavage being warmed to a liquid pulmonary lavage effluent;

concurrently removing said liquid pulmonary effluent from said subject's tracheobronchial tree via a second flexible catheter which is inserted into said subject's tracheobronchial tree substantially parallel to said first catheter and having a closed distal end and a proximal end, and having a plurality of openings adjacent said proximal end of said catheter, said openings providing access to the interior of said catheter through which said liquid pulmonary lavage effluent flows into an effluent reservoir;

said effluent reservoir containing means for creating low pressure to withdraw said liquid pulmonary lavage effluent from the subject's tracheobronchial tree;

filtering and purifying said liquid pulmonary lavage effluent to form a recycled liquid pulmonary lavage in said effluent reservoir and passing said product to said reservoir.

16. The method defined in claim 15 wherein the total dose of said fluid instilled into said subject is 25 cc of said fluid per kilogram of body weight.

* * * * *